United States Patent [19]
McCarthy Smith

[11] Patent Number: 5,940,886
[45] Date of Patent: Aug. 24, 1999

[54] SLEEP SHADE

[75] Inventor: Colleen McCarthy Smith, 25212 Calero Ave., Laguna, Hills, Calif. 92653

[73] Assignee: Colleen McCarthy Smith, Laguna Hills, Calif.

[21] Appl. No.: 09/004,950

[22] Filed: Jan. 9, 1998

[51] Int. Cl.$^6$ .................................................. A61F 9/04
[52] U.S. Cl. ........................................... 2/206; 2/9; 2/15
[58] Field of Search .............................. 2/9, 206, 11, 15; 132/319

[56] References Cited

U.S. PATENT DOCUMENTS

| | | | |
|---|---|---|---|
| 194,815 | 9/1877 | Emerson-French | 2/206 |
| 438,800 | 10/1890 | Cassidy | 2/206 |
| 780,616 | 1/1905 | Palmer | 2/206 |
| 1,627,523 | 5/1927 | Morris | 2/9 |
| 2,671,446 | 3/1954 | Mann | 2/206 |
| 2,942,270 | 6/1960 | Enright | 2/15 |
| 4,886,079 | 12/1989 | Mooney | 2/206 |
| 5,634,210 | 6/1997 | King et al. | 2/9 |

Primary Examiner—Diana L. Oleksa
Attorney, Agent, or Firm—Myers, Dawes & Andras

[57] ABSTRACT

A sleep shade is adapted to be worn by a person having a face with eyes, nose and a mouth having both an open state and a closed state. The shade includes an eye section forming a seal with the eyes of the person, the eye section including an eye cover. The nose section is coupled to the eye section and adapted to receive the nose of the person, the nose section including at least one opening in proximity to the nose of the person. A mouth section is coupled to the nose section and includes a mouth cover having a length sufficient to cover the mouth of the person in both the open state and the closed state. A suitable headband is coupled to at least one of the sections to hold the sections against the head of the person.

7 Claims, 2 Drawing Sheets

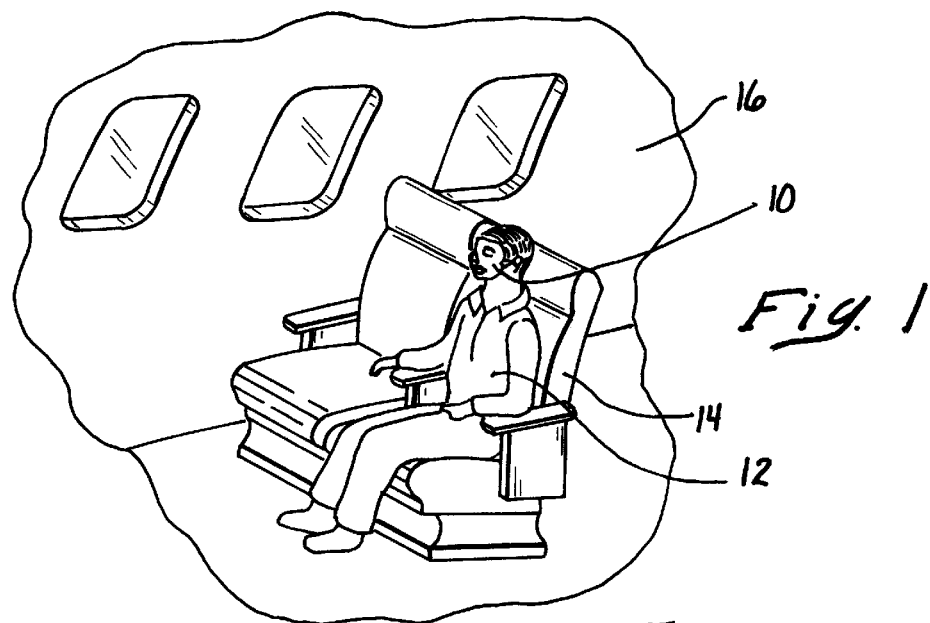
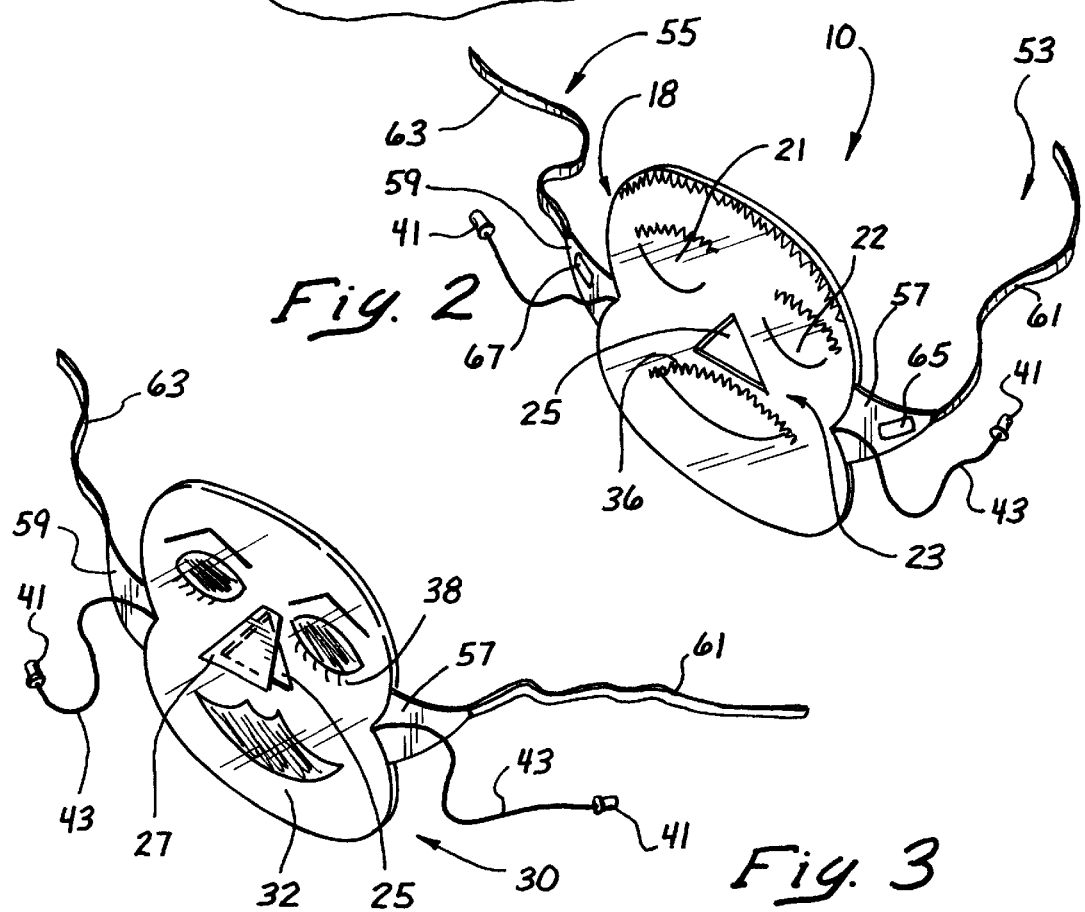

SLEEP SHADE

BACKGROUND OF THE INVENTION

1. Field of the Invention

This invention relates generally to sleep shades and more specifically to shades adapted to be worn by a user and having properties for inhibiting the passage of light through the shade to the eyes of the user.

2. Discussion of the Prior Art

There are many instances in life when one must patiently sit and wait for an event to occur. Typical of these instances is the situation where a passenger on an airplane or train must sit and wait his or her arrival at the destination. When long periods of time are encountered under these circumstances, one can become extremely bored. It is not uncommon under these circumstances for an individual to attempt to sleep in order to pass the seemingly endless time in a state of semi-unconsciousness. One would hope that such a nap could result in deep sleep over several hours leaving the person rested upon their arrival at the destination.

Unfortunately, sleeping traits vary and many people suffer from habits which they deem to be less than sociable. For example, a person in the sleeping state will often relax their jaw so that their mouth gapes open. Snoring is also common under these circumstances. It is the persons perception of these habits which often make them want to maintain some degree of consciousness. This of course interferes with the ultimate desire to sleep deeply for a prolonged period of time.

SUMMARY OF THE INVENTION

In accordance with the present invention, a sleep shade is provided not only with an eye section for inhibiting the transmission of light to the eyes of the user, but also a nose section which facilitates breathing, and a mouth section which covers the mouth of the user. The resulting sleep shade inhibit the visual as well as audible aspects of various sleeping habits. By providing the sleep shade with a mouth section, a gaping mouth is not noticeable and there may even be some muffling of snoring sounds.

Various accessories can also be provided for the sleep shade to otherwise facilitate the sleeping experience. For example, earplugs may be provided and attached directly to the mask. Special pockets can even be provided in the mask to store the earplugs. A foam liner can be provided for various purposes to improve the comfort of the user, as well as to facilitate the light-blocking and noise-muffling aspects of the sleep shade.

The sleep shade may be formed with a generally thick padded configuration or provided in a relative thin flexible form. In the latter regard, a foldable handkerchief-type shade might be used to cover the eyes, nose and mouth of the user. The shade can be attached to the head of the user, using one or more ties, elastic bands, straps and buckles as well known in the art. The mask can be scented to render it more pleasing to the users or those in the vicinity of the user. The shade can also be printed with indicia illustrating, for example, closed eyes, the gender of the user, a supported sports team, or a school logo. The resulting sleep shade should enhance every aspect of the sleeping experience, resulting in deeper and prolonged sleep.

In one aspect of the invention, the sleep shade includes an eye section forming a seal with the face of the user in order to inhibit the passage of light to the eyes of the user, the eye section including a pair of eye covers disposed in proximity to the eyes of the user. A nose section is coupled to the eye section and adapted to receive the nose of the user. The nose section includes at least one opening in proximity to the nose of the user. A mouth section coupled to the nose section includes a mouth cover disposed in proximity to the mouth of the user. The mouth cover is provided with a length sufficient to cover the mouth of the user in an open state. A headband is coupled to at least one of the sections and provided with a size and configuration for holding the sections in proximity to the face of the user.

These and other features and advantages of the invention will become more apparent with a discussion of preferred embodiments in reference to the associated drawings.

DESCRIPTION OF THE DRAWINGS

FIG. 1 is a perspective view illustrating an airline passenger using a sleep shade of the present invention;

FIG. 2 is perspective view of one embodiment of a sleep shade carrying male gender indicia on the front thereof;

FIG. 3 is a perspective view of an additional embodiment of the invention carrying female gender indicia on the front thereof;

DESCRIPTION OF THE PREFERRED EMBODIMENTS AND BEST MODE OF THE INVENTION

Figure 4:
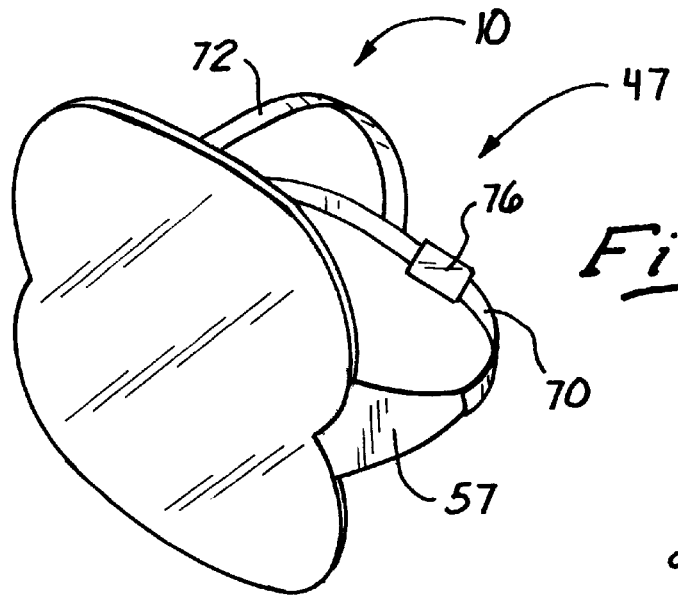
FIG. 4 is a perspective view illustrating a head strap configuration of particular advantage to the present invention.

A sleep shade as illustrated in FIG. 1 and designated generally by the reference numeral 10. The sleep shade is shown to be operatively disposed over the face of a user, in this case, an airline passenger 12 napping on a seat 14 of an airplane 16. It will initially be noted that the airplane 16 is merely representative of a typical environment wherein a person, such as the passenger 12, may choose to take a nap in a public place.

The sleep shade 10, illustrated in greater detail in FIG. 2, will typically include an eye section 18 forming a seal with the face of the passenger 12 in order to inhibit the passage of light to the eyes of the person. This eye section 18 will typically include eye covers 21, 22 which are disposed in proximity to the eyes of the passenger 12. The eye covers 21, 22 are intended to be generally opaque thereby providing a barrier to the passage of ambient light through the sleep shade 10 to the eyes of the passenger 12.

A nose section 23 is provided in juxtaposition to the eye section 18 and is sized and configured to receive the nose of the passenger 12. The nose section 23 may be formed as an opening 25 through which the nose extends. Alternatively, a hinged flap (not shown) may be provided so that the nose extends through the opening 25 and is generally covered by the flap. As a further alternative, the nose section may be a formed structure 27 as illustrated in FIG. 3. This formed structure would provide a cavity for the nose of the passenger 12. The advantage of this structure 27 is that it could be formed from an opaque material thereby inhibiting the passage of light through the nose section 23 to the eyes of the passenger 12.

Importantly, the sleep shade 10 includes a mouth section 30 which can be coupled to the nose section 23. This mouth section 30 includes a mouth cover 31 disposed in proximity to the mouth of the person, such as the passenger 12. The mouth cover 31 in a preferred embodiment has a length sufficient to cover the mouth of the passenger 12 whether the mouth is in a closed state or an open state.

This mouth section 30 is of particular advantage to the present invention as it provides a cover for the mouth of the passenger 12 who will typically be sleeping in a public environment. It is well known that many people in a state of slumber will relax their jaw so that the mouth tends to gape open. This is generally perceived to be unsightly and therefore embarrassing in a public environment. A gapping mouth also promotes snoring which may be equally offensive in a public environment. With a mouth section 30 providing at least a visual cover for the mouth, even in an open or gaping state, the sleep shade 10 overcomes the primary objection of sleeping in a public environment. Thus the sleep shade 10 encourages the passenger 12 to sleep deeply over a longer duration without regard to the potential embarrassment of sleeping habits.

The novelty of the sleep shade 10 can be enhanced by providing indicia 34 on the front of the sleep shade 10. For example, the face of a sleeping man including a moustache 36 could form the indicia 34 as illustrated in FIG. 2. Alternatively, the indicia 34 may include the face of a female gender, including long eyelashes 38.

In order to further enhance the sleeping experience, the sleep shade 10 can be provided with earplugs 41 which can be attached by strings or elastic members 42, for example at the nose section 23. In the illustrated embodiment, a head engagement structure is provided in the form of a pair of ties 43, 45, each including a cheek pad 57, 59 and an associated tying member 61, 63. In a preferred embodiment, a pair of pockets 65, 67 are provided in the associated cheek pads 57, 59 to store the earplugs 41.

Alternatively, the head engagement mechanism 47 may include elastic straps, including for example a back-of-the-head strap 70 and a top-of-the-head strap 72. A further alternative might be to provide only the back-of-the-head strap 70 formed of nonelastic members joined by a coupling device 76.

Figure 5:
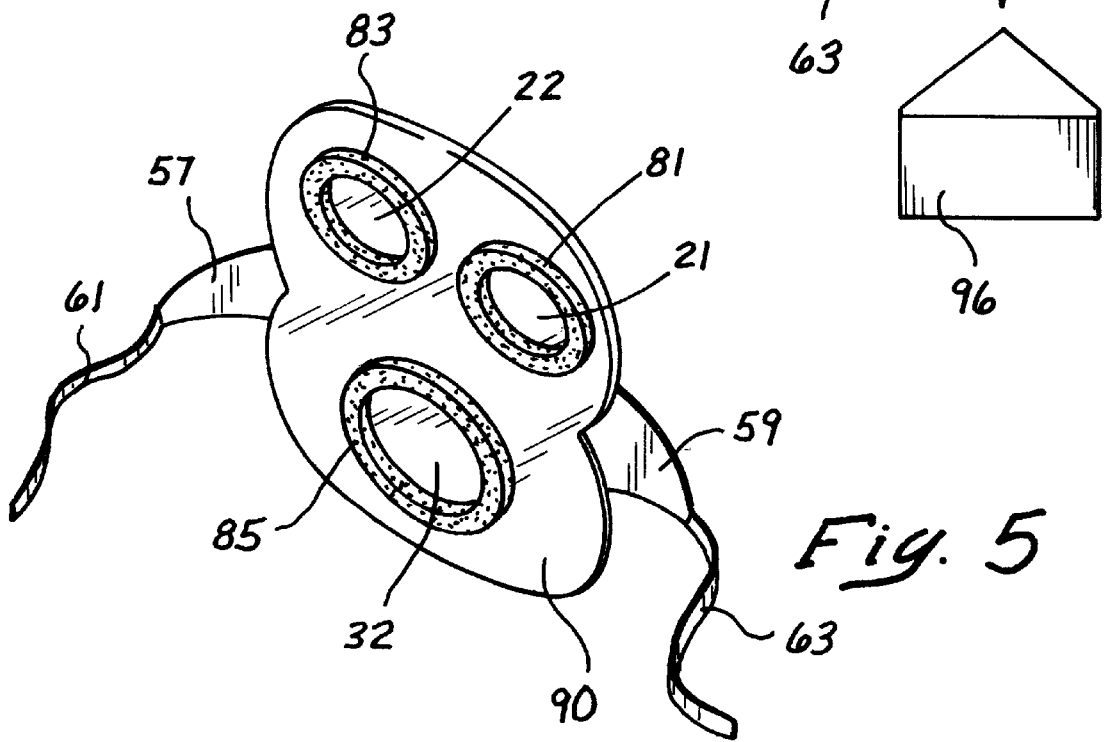
FIG. 5 is a back perspective view of a sleep shade including foam padding and barriers.

A back view of the sleep shade 10 is illustrated in FIG. 5 where surrounding resilient pads 81, 83 and 85 are provided for the respective eye covers 21, 22 and the mouth cover 32. These pads 81, 83, 85 can serve several functions for the sleep shade 10. In a preferred embodiment, the pads 81, 83, 85 are formed of a soft resilient material such as foam and provided with sufficient depth that it is primarily these pads 81, 83, 85 which provide the sole contact with the face of the passenger 12. In addition to providing a soft, resilient contacting material, the eye pads 81, 83 associated with the eye covers 21, 22, aid in providing a opaque barrier so that light outside of the pads 81, 83 does not pass to the eyes of the passenger 12. In the same manner as the eye pads 81 and 83 provide optical barriers for the eyes of the passenger 12, the resilient pad 85 associated with the mouth cover 32 provides an audio barrier for the mouth of the passenger 12. Thus, the resilient pad 85 forms a seal around the mouth thereby inhibiting audible sounds such as snoring which might be objectionable in a public environment.

In the foregoing embodiments, the eye section 18, nose section 23, and mouth section 30 are formed integrally of a substrate 90 which will generally have a rigid or semirigid configuration. Typically this substrate 90 will be provided with a permanent form having the configuration of a typical face. The resilient pads 81, 83, 85 can be glued to the back of the substrate 90. Alternatively or in combination with the pads 81, 83, 85, the shade 10 may be provided with other types of padding facilitating barriers to visible light and audible sound.

Figure 6:
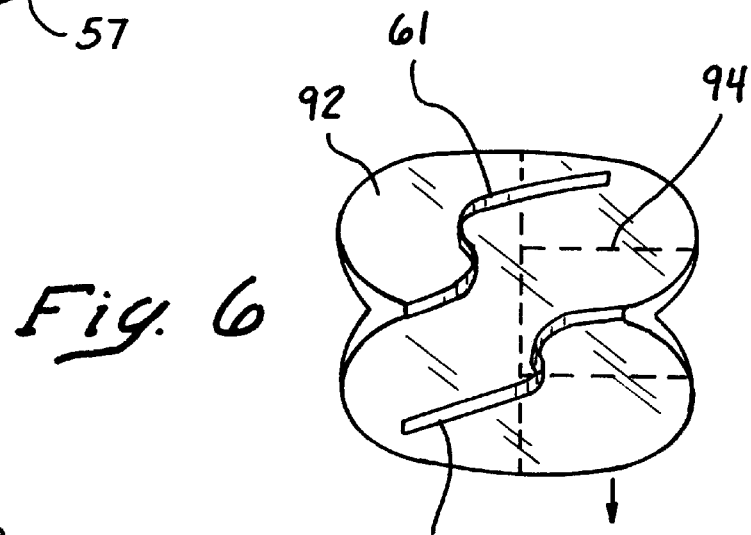
FIG. 6 is a front elevation view illustrating a cloth embodiment of the sleep shade suitable for folding and carrying in a small pouch.

A further embodiment of sleep shade 10 is formed of a flexible fabric 92 which can be easily folded, for example along dotted lines 94, into a compact configuration and carried in a pouch 96 as illustrated in FIG. 6.

It will be apparent that many variations may occur within the concept of the present invention. For example, the substrate 90 can be formed of many different materials and configured in substantially any shape that will facilitate the visual and/or audible barriers contemplated. Many different head engagement mechanisms could be adapted for use to hold the substrate 90 over the face of the passenger 12. The resilient pads 81, 83, 85 can also vary significantly in their shape and design in order to facilitate their functional purposes.

Given these wide variations, which are all within the scope of this concept, one is cautioned not to restrict the invention to the embodiments which have been specifically disclosed and illustrated, but rather encouraged to determine the scope of the invention only with reference to the following claims.

I claim:

1. A sleep shade adapted to facilitate sleep for a person having a pair of eyes, a nose and a mouth with an open state and a closed state, the sleep shade to be worn by the person and comprising:

a mask having a front portion for facing outwardly from a person and a back portion for facing inwardly toward the person, the mask including
an eye section including an eye cover adapted for placement over the eyes of a person,
a nose section coupled to the eye section and adapted to receive the nose of a person, the nose section including at least one opening adapted for placement over the nose of a person, and
a mouth section coupled to the nose section and including a mouth cover adapted for placement over the mouth of a person, the mouth cover having a length sufficient to cover the mouth of the person in both the open state and the closed state;

spacing means secured to the back portion of the mask proximate the eye section for spacing the mask from the face of a person to allow air to circulate between the mask and the face, the spacing means being formed of a resilient material for forming a seal with the face of a person to inhibit the passage of light to the eyes of a person; and a headband coupled to at least one of the eye section, nose section and mouth section and having a size and configuration for holding the sections on the head of a person.

2. The sleep shade recited in claim 1, wherein the spacing means comprises at least one resilient pad configured to encircle the eyes of a person.

3. The sleep shade recited in claim 2, further comprising secondary spacing means secured to the back portion of the mask proximate the mouth section, the secondary spacing means being formed of a resilient material for forming a seal around the mouth of a person to muffle audible sounds from the mouth of a person.

4. The sleep shade recited in claim 3, wherein the secondary spacing means comprises at least one resilient pad configured to encircle the mouth of a person.

5. The sleep shade recited in claim 1, wherein the headband comprises:

an elastic band coupled to the eye section and adapted to extend at least partially around the head of a person.

6. The sleep shade recited in claim 1, further comprising:

indicia disposed on the front portion of the mask and adapted to provide a visual indication that a wearer is attempting to sleep.

7. The sleep shade recited in claim 1, further comprising:

ear plugs coupled to one of the eye section, the nose section, the mouth section, and the headband.

* * * * *